United States Patent
Hansmann et al.

(10) Patent No.: US 9,459,151 B2
(45) Date of Patent: ***Oct. 4, 2016

(54) GAS MEASUREMENT SYSTEM

(71) Applicant: DRÄGER SAFETY AG & CO. KGaA, Lübeck (DE)

(72) Inventors: Hans-Ullrich Hansmann, Barnitz (DE); Andreas Mohrmann, Krummesse (DE); Arne Tröllsch, Lübeck (DE); Rainer Polzius, Lübeck (DE)

(73) Assignee: DRÄGER SAFETY AG & CO. KGaA, Lübeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,323

(22) PCT Filed: Jul. 17, 2013

(86) PCT No.: PCT/EP2013/065101
§ 371 (c)(1),
(2) Date: Jan. 16, 2015

(87) PCT Pub. No.: WO2014/012977
PCT Pub. Date: Jan. 23, 2014

(65) Prior Publication Data
US 2015/0192470 A1    Jul. 9, 2015

(30) Foreign Application Priority Data

Jul. 20, 2012  (DE) .................. 10 2012 014 504

(51) Int. Cl.
*G01N 21/00* (2006.01)
*G01J 3/50* (2006.01)
(Continued)

(52) U.S. Cl.
CPC .............. *G01J 3/501* (2013.01); *G01J 3/0202* (2013.01); *G01J 3/0267* (2013.01); *G01J 3/0289* (2013.01);
(Continued)

(58) Field of Classification Search
CPC .............. G01J 3/02; G01J 3/501; G01J 3/51; G01N 15/1459; G01N 21/65
USPC ..................................... 356/72–73
See application file for complete search history.

(56) References Cited

U.S. PATENT DOCUMENTS 4,123,227 A   10/1978  Heim et al.
5,089,232 A   2/1992   May
(Continued)

FOREIGN PATENT DOCUMENTS

CN    2263343 Y   9/1997
CN    1865943 A   11/2006
(Continued)

*Primary Examiner* — Abdullahi Nur
(74) *Attorney, Agent, or Firm* — McGlew and Tuttle, P.C.

(57) ABSTRACT

A gas measurement system for measuring the concentration of gaseous and/or vaporous components of a gas mixture by means of a color change of at least one reaction substance on a reaction support unit, which is arranged in at least two light permeable channels in such a manner that the color change on the reaction substance can be detected at low expense on a large number of separate positions. The detecting unit which detects the color change can be designed as a digital camera with an electronic image converter or image sensor, and an imaging optics system (e.g., a lens system). Related systems, methods, apparatus, and articles are also described.

45 Claims, 5 Drawing Sheets

Figure 1:
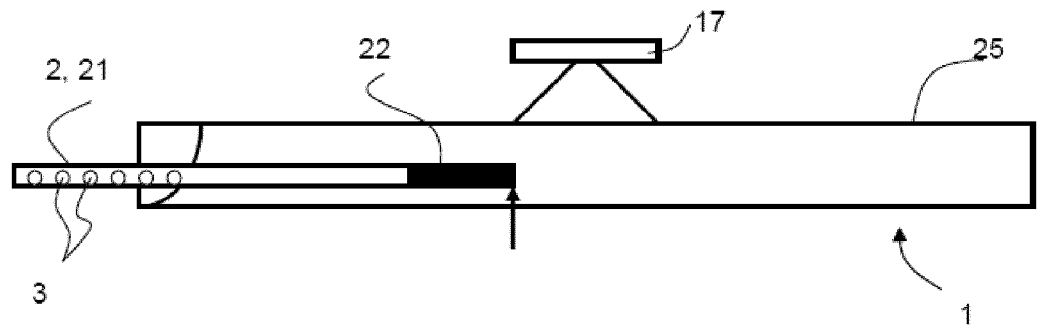

(51) Int. Cl.
  *G01N 21/05* (2006.01)
  *G01N 21/78* (2006.01)
  *G01J 3/02* (2006.01)
  *G01N 21/77* (2006.01)

(52) U.S. Cl.
  CPC ............ *G01J 3/0291* (2013.01); *G01N 21/05* (2013.01); *G01N 21/783* (2013.01); *G01N 2021/7763* (2013.01)

(56) References Cited

U.S. PATENT DOCUMENTS

| | | |
|---|---|---|
| 5,397,538 A | 3/1995 | Stark et al. |
| 5,464,588 A | 11/1995 | Baether et al. |
| 5,468,645 A | 11/1995 | Kirollos et al. |
| 6,266,998 B1 | 7/2001 | Hackenberg |
| 6,652,811 B1 | 11/2003 | Pooch et al. |
| 6,902,934 B1 | 6/2005 | Bergh et al. |
| 7,122,156 B2 | 10/2006 | Bergh et al. |
| 2005/0196322 A1 | 9/2005 | Truex et al. |
| 2015/0168307 A1* | 6/2015 | Kuck ................. G01N 21/05 436/130 |

FOREIGN PATENT DOCUMENTS

| | | |
|---|---|---|
| CN | 102 517 196 A | 6/2012 |
| DE | 26 28 790 B1 | 11/1977 |
| DE | 28 40 867 A1 | 4/1980 |
| DE | 37 09 296 C1 | 9/1988 |
| DE | 39 02 402 C1 | 6/1990 |
| DE | 43 03 861 A1 | 8/1994 |
| DE | 43 45 151 A1 | 8/1994 |
| DE | 44 15 866 C1 | 6/1995 |
| DE | 43 03 858 C2 | 8/1995 |
| EP | 0 266 628 A2 | 5/1988 |
| EP | 0 610 673 A1 | 8/1994 |
| EP | 0 646 784 A1 | 4/1995 |
| GB | 2 183 830 A | 6/1987 |

\* cited by examiner

GAS MEASUREMENT SYSTEM

TECHNICAL FIELD

The current subject matter is directed to a gas measurement system using a digital camera to characterize gases passing therethrough.

BACKGROUND

Gas measurement systems are used for measuring the concentration of gas and/or vaporous components of a gas mixture by means of a color change of at least one reaction substance. On a reaction support unit with a chip or a plate, transparent glass tubes are arranged on the chip. The same or a different reaction substance is arranged within the glass tube. A remaining gas measurement system comprises a suction pump for conveying the gas mixture through the glass tube and thus to the reaction substance as well as a mechanical bearing in the form of friction bearing for the reaction support unit. Here, the reaction support unit is introduced first as an exchangeable unit into the remaining gas measurement system, and then the reaction support unit is moved by a servomotor into a predetermined position. Through a gas connector, the gas mixture is conveyed through the gas tube by the suction pump, and in the case of the presence of gaseous and/or vaporous components on which the reaction substance produces a color change, a color change of the reaction substance occurs. This color change is detected by an optoelectronic detection device, namely a number, for example, 6 Si diodes. As a result, the color change of the reaction substance on the glass tube can be detected, disadvantageously, at only six positions of the reaction substance. Here, an evaluating unit can evaluate the data of only six separate color change positions of the reaction substance. The accuracy and the reliability of the gaseous and/or vaporous components detected by the gas measurement system are consequently low. Such gas measurement systems are used, for example, at work sites, in special waste dumps, or in the case of accidents involving chemicals, in order to be able to rapidly detect outflowing noxious substances of unknown type and concentration on site.

DE 39 02 402 C1 shows a device for measuring the concentration of gaseous and/or vaporous components of a gas mixture using optically detectable reaction zones of gas test tubes containing a substance that reacts with the a component to be detected, wherein the change of the reaction zone can be determined by direct observation and/or by an optoelectronic scanning device. Here, several channels are arranged on a support in chip form that is exchangeable and insertable in an optoelectronic scanning device. The scanning device is designed here as an LED array.

DE 43 03 858 C2 shows a device for the colorimetric detection of gaseous and/or vaporous components of a gas mixture on the basis of a discoloration of a reaction zone arranged in a channel, one or more of which are applied on a transparent support in disk form which can be moved into an evaluation position which is detected by a signal transmission unit in a signal receiving unit. A barcode as data field is also arranged on the support. The signal receiving units here are designed as CCD sensors. For example, they can be silicon photodiodes or silicon transistors.

The problem of the present invention therefore consists in providing a gas measurement system and a method for operating a respiration and anesthesia apparatus, in which the color change on the reaction substance can be detected at a large number of separate positions at low technical expense.

SUMMARY

The current subject matter provides many advantages. For example, the current subject matter provides a gas measurement system and a method for operating a respiration and anesthesia apparatus, in which the color change on the reaction substance can be detected at a large number of separate positions at low technical expense.

These advantages can be provided by a gas measurement system or by a gas measurement arrangement for measuring the concentration of gaseous and/or vaporous components of a gas mixture by means of a color change of at least one reaction substance on a reaction support unit, wherein the at least one reaction substance is arranged on the reaction support unit separately within at least two light permeable channels, the gas measurement system comprising a gas conveyance device for conveying the gas mixture through a channel and to the at least one reaction substance, a mechanical bearing, in particular a friction bearing, for the reaction support unit, for example, a motor for moving the reaction support unit or another component, so that the gas mixture can be conveyed separately through one of the at least two channels, an optoelectronic detection device for detecting a color change of the at least one reaction substance during and/or after the conveyance of the gas mixture through a channel, wherein, in the direction of flow of the gas mixture through the channel, the color change can be detected in at least two separate positions, an evaluating device for evaluating the data acquired by the optoelectronic detection unit, and an optical and/or acoustic display device for displaying the data evaluated by the evaluating unit, wherein the optoelectronic detection device is designed as a digital camera with an electronic image converter or image sensor, and an imaging optics system (e.g., a lens system, etc.).

The gas measurement system or a gas measurement arrangement as remaining gas measurement system comprises the gas conveyance device, the mechanical bearing (e.g., a motor, etc.) the digital camera, the evaluating device and the optical and/or acoustic display device. The reaction support unit can be introduced as an exchangeable unit into the remaining gas measurement system or the gas measurement arrangement. The gas measurement system or the remaining gas measurement system here has a digital camera for the detection of the color change of the reaction substances or of the reaction substance within the glass tube. As a result, at low technical expense, the color changes can be detected at a very large number of separate positions of the reaction substance within the glass tube, and subsequently evaluated by the evaluating device. This allows a particularly precise and reliable detection of the concentration of the gaseous and/or vaporous components. A digital camera has a large pixel number, so that by means of the evaluation of the data detected by the digital camera, using appropriate optical software or optical evaluation software on the evaluating device, the color changes on the reaction substance can be detected at a very large number of separate positions. Due to these color changes, in particularly the course over time of the color changes, at the separate positions of the reaction substance, the type and/or the concentration of the gaseous and/or vaporous components can be determined. Here, in general, first the dependency on time of the color changes at the very large number of separate positions is detected by the digital camera and stored in a data storage device, and it is only after the complete termination of the color changes due to the gas mixture being passed through that the evaluation by means of the evaluating device occurs.

In particular, the digital camera is designed as a camera chip, particularly a CMOS camera chip. A camera chip is particularly simple and cost effective in the manufacture and it requires little installation space on the gas measurement system or the remaining gas measurement system or the gas measurement arrangement.

In a further embodiment, the gas measurement system comprises a transmission device, for example, an LED, for the emission of electromagnetic radiation, so that, with the electromagnetic radiation, it is possible to radiate through and/or onto the at least one reaction substance, and/or the gas measurement system comprises a housing, and the housing can form, in addition, the friction bearing for the reaction support unit. By means of the transmission device, the radiation is applied onto or through the reaction substance, so that as a result color changes on the reaction substance can be detected particularly precisely by the digital camera.

In an additional embodiment, the gas conveyance device is designed as a pump, particularly a suction pump, and/or the gas measurement system comprises a gas connector which can be moved between two positions, and connected fluidically to the gas conveyance device, so that, in a first position of the gas connector, no fluidic connection exists between the gas connector and the channel, and in a second position of the gas connector a fluidic connection exists between the gas connector and the channel.

The motor can be designed as an electric motor, particularly a servomotor, and the motor can be brought by means of a driving roller into effective mechanical connection with the reaction support unit, and/or the evaluating device comprises a processor, for example, a microcontroller, and a data storage device, and/or the display device comprises a monitor and/or a light emitter, for example, a lamp or an LED, and/or a signal tone generator.

In a variant, the gas measurement system or the remaining gas measurement system, in addition to the remaining gas measurement system, comprises the reaction support unit and the reaction support unit can comprise a chip or a plate, and tubes (e.g., glass tubes, etc.), arranged on the chip or the plate, which delimit the channels, and the at least one reaction substance is arranged within the tubes. On the gas measurement arrangement or the remaining gas measurement system, the reaction support unit is arranged, and the remaining gas measurement system or the gas measurement arrangement together with the reaction support unit forms the gas measurement system.

Advantageously, the reaction support unit comprises a coding, for example, a coding that can be read out optically, in particular a matrix coding, or a RFID chip, and/or the reaction support unit contains at least two indicator pins which can be moved between two positions, and one indicator pin is associated with each tube, so that, in the first position of the indicator pin, the reaction substance which has not been exposed to the gas mixture can be displayed within the associated tube, and, in the second position of the indicator pin, the reaction substance which has been exposed to the gas mixture within the associated tube can be displayed and/or the digital camera is arranged at a distance between 2 and 50 mm, particularly between 15 and 20 mm, from the tube, which is detected by the digital camera. The coding comprises in particular data pertaining to the reaction substance and/or the number of tubes on the reaction support unit. Depending on these data on the reaction substance, which are stored on the coding or in the RFID chip, for different reaction support units with different reaction substances in the tubes, the evaluation of the data acquired by the digital camera is carried out by the evaluating device.

In a further embodiment, a method described in this patent application can be carried out by the gas measurement system.

Method for operating a gas measurement system, in particular a gas measurement system described in this patent application, can include: moving a reaction support unit or another component with a motor, conveying a gas mixture through a, particularly only one, channel with a reaction substance by means of a gas conveyance device, detecting by means of an optoelectronic detection device a color change of the at least one reaction substance during and/or after the conveyance of the gas mixture through the channel, wherein in the direction of flow of the gas mixture through the channel the color change is detected in at least two separate positions, evaluating the data detected by the optoelectronic detection device with regard to the color change by means of an evaluating device, optical and/or acoustic display of the data evaluated by the evaluating device by means of a display device, wherein the color change is detected with a digital camera.

In particular, the digital camera acquires, particularly exclusively, the colors red, green and blue, and/or the digital camera, particularly only one digital camera, detects, in the direction of flow of the gas mixture, through the channel, in a large number separate positions, for example, at least 5, 10, 50, 100 or 500 separate positions, the color change separately, and/or the digital camera detects the course over time of the color change during and/or after the conveyance of the gas mixture through the channel, and said course can be stored in an evaluation data storage device, and/or the digital camera, in particular only one digital camera, detects the color change on the reaction substance on a fictitious line in the direction of flow of the gas mixture over the entire fictitious line. The imaging optics system or the distance of the camera from the tube is configured to make it possible for the digital camera to detect the entire tube with the reaction substance, so that, in the direction of flow of the gas mixture on a fictitious line, this entire fictitious line can be detected with regard to the color change, i.e., there is no area of the reaction substance in the direction flow of the gas mixture where no determination of the color change by the digital camera occurs.

In a further embodiment, the digital camera detects the position of the reaction support unit moved by the motor, by evaluating data from an image sensor of the digital camera, particularly by means of appropriate software on the evaluating device, and the motor can be controlled depending on the position detected by the digital camera.

In an additional variant, for the fluidic connection of the gas conveyance device to the channel, a gas connector is moved to, on or in the channel, and/or before and/or during the conveyance of the gas mixture, an indicator pin associated with the channel is moved through the channel on the reaction support unit from a first position to a second position, in particular by bringing the gas connector in contact with the indicator pin during a movement of the gas connector, so that as a result the indicator pin is moved, in particular pushed, from the first position into the second position.

In a further variant, the digital camera detects the position of the indicator pin in order to detect in this manner whether no gas mixture has been passed through the channel with the reaction substance associated with the indicator pin, or that a gas mixture has already been passed through. The indicator pin here has a different color than the remaining the reaction support unit, in particular the chip or plate, and as a result it is possible for the digital camera to detect, using two corresponding different ROI (region of interest), the first and second position of the indicator pin. Based on the appropriate assignment of an indicator pin to each tube, this allows the digital camera to optically detect in a simple manner whether a gas mixture has already been passed through a tube or not. Consequently, it is possible to easily detect whether a tube has already been used for measuring the components.

In a further embodiment, the digital camera reads out an optical coding, particularly a matrix coding, on the reaction support unit, and, as a function of the data stored in the coding, the color change of the reaction substance detected by the digital camera is evaluated. The gas measurement system thus advantageously does not require an additional device for reading out the optical coding.

In particular, the reaction support unit is introduced, for example, inserted or pushed, into the remaining gas measurement system, and this is detected by the digital camera, subsequently the optical coding is read out by the digital camera, and/or, depending on the position detected by the digital camera, and also based on the detection of the position of the indicator pin, the motor is also controlled so that the reaction support unit is moved into a position, in which, in case of a movement of the gas connector, the gas connector is brought into fluidic connection with a channel through which no gas mixture has been led.

In another interrelated aspect, an apparatus can include a housing, a friction bearing, a gas conveyance device, an optoelectronic device, an evaluating device, and a sensory feedback device. The housing defines a slot. The friction bearing is positioned within the slot and is configured to couple to a reaction support unit that includes at least two light permeable channels configured to receive at least one reaction substance, the at least one reaction substance changing color in presence of at least one particular gaseous or vaporous component. The gas conveyance device is configured to convey gas through at least one channel of the reaction support unit. The optoelectronic detection device is configured to detect a color change of the at least one reaction substance on the reaction support unit during and/or after the conveyance of the gas mixture, the color change being detected in the direction of flow of the gas mixture through the at least two channels in at least two separate positions. The optoelectronic detecting device includes a digital camera having an image converter or an imaging optics system. The evaluating device evaluates the data detected by the optoelectronic detection device. The sensory feedback device (e.g., display, speaker, etc.) provides sensory feedback characterizing the data evaluated by the evaluating device.

In a further interrelated aspect, a method can include: moving a reaction support unit through a gas measurement system, the reaction support unit having a plurality of channels each with at least one reaction substance; conveying, using a gas conveyance device, a gas mixture through a single channel of the reaction support unit; detecting, using a digital camera of an optoelectronic detection device, a color change of the at least one reaction substance during and/or after the conveyance of the gas mixture through the channel, wherein the color change is detected in the direction of flow of the gas mixture through the channel in at least two separate positions; evaluating, using an evaluating device, data acquired by the optoelectronic detection device with regard to the color change; and providing, using a sensory feedback device, sensory feedback regarding the evaluated data.

Advantageously, identical reaction substances for identical gaseous and/or vaporous components or different reaction substances for different gaseous and/or vaporous components are arranged in the channels. In the case of identical reaction substances on the reaction support unit, the reaction support unit can not only be used to detect identical gaseous and/or vaporous components, but the reaction support unit can also be used to detect different gaseous and/or vaporous components in the case of different reaction substances on the reaction support unit.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF THE ACCOMPANYING FIGURES

Figure 2:
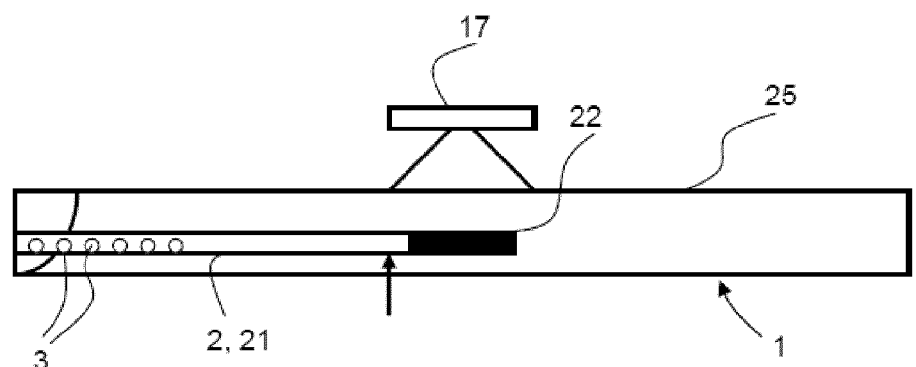
Figure 3:
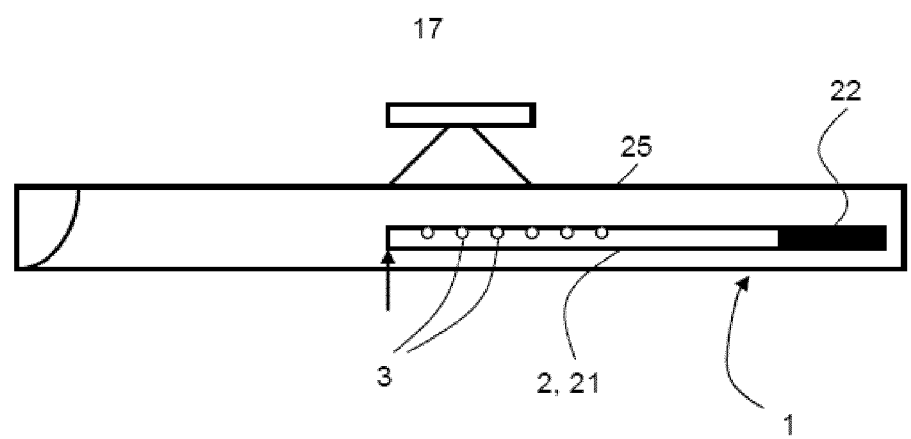
Figure 4:
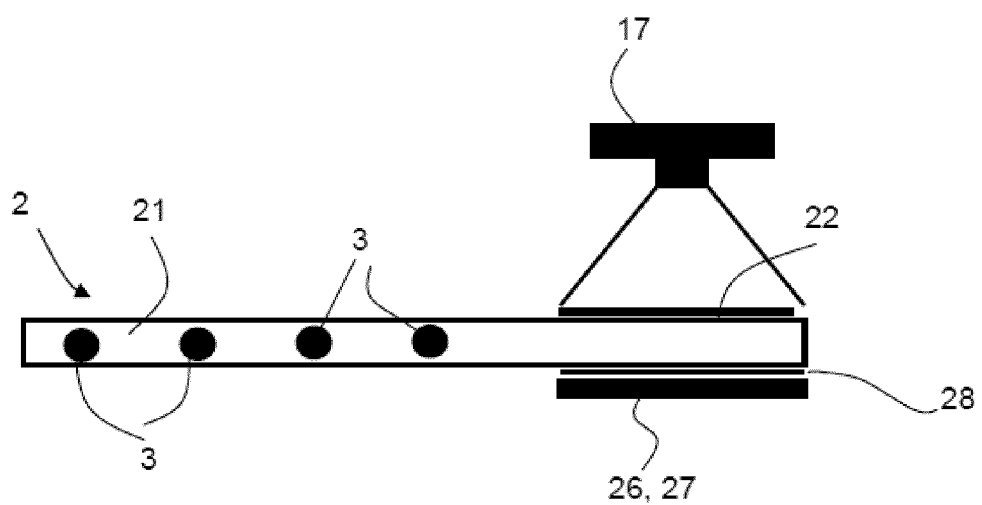
Figure 5:
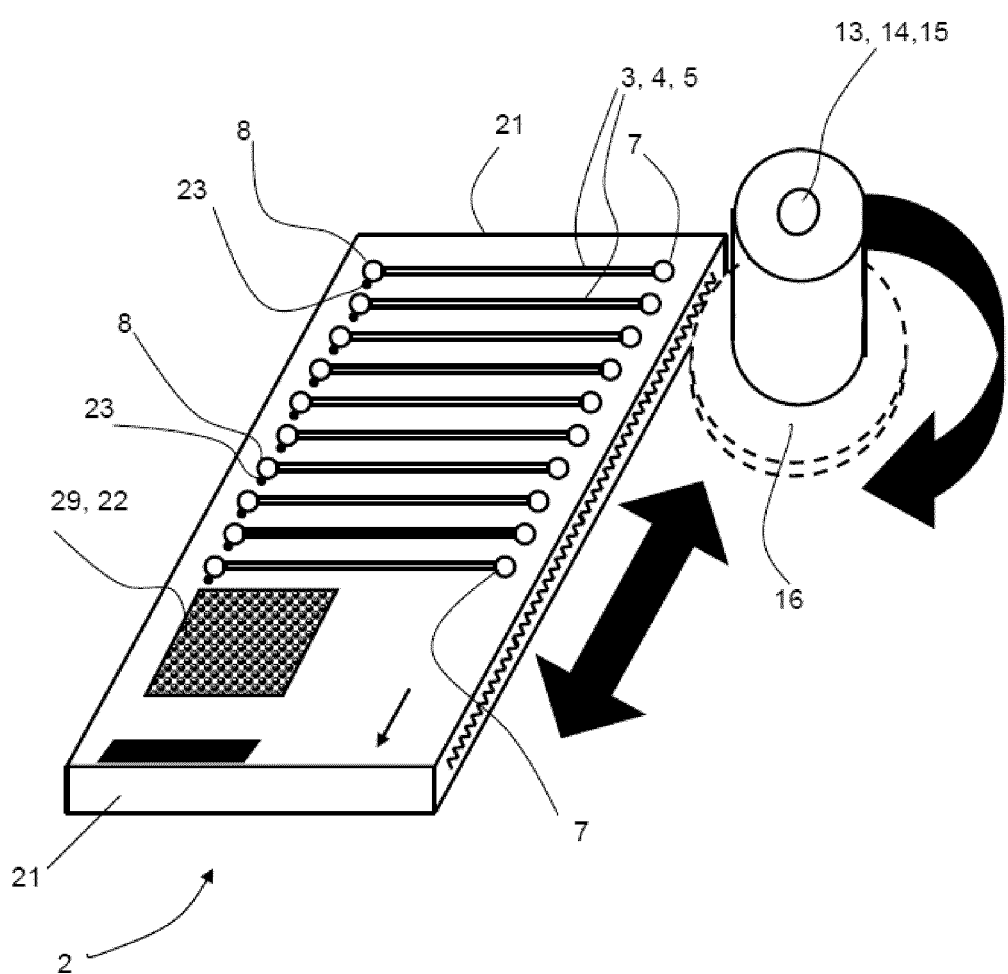
Figure 6:
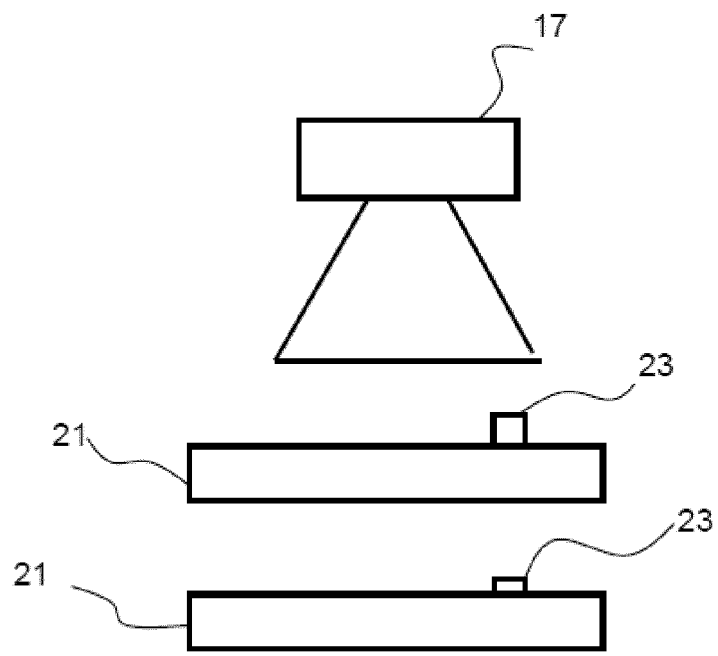
Figure 7:
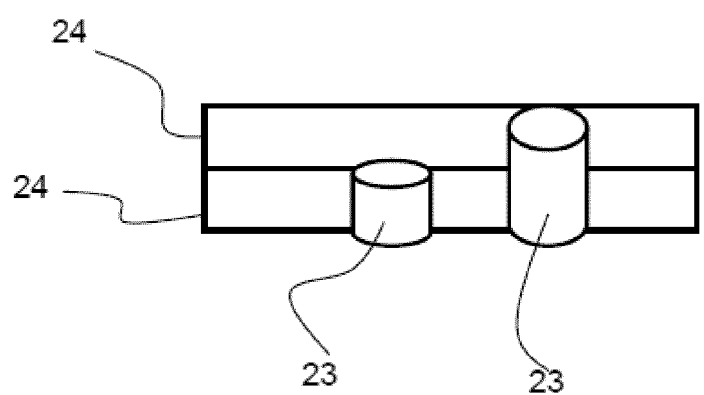
Figure 8:
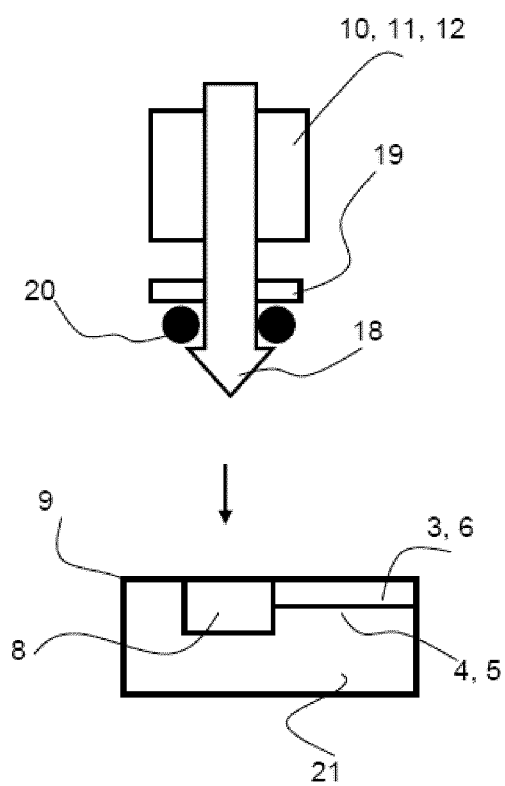
Figure 9:
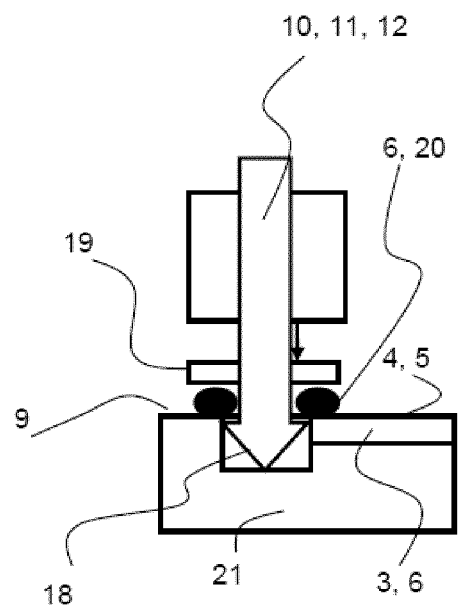

FIG. 1 shows a highly simplified longitudinal section of a gas measurement system during a manual insertion of a reaction support unit into a housing, FIG. 2 shows a highly simplified longitudinal section of the gas measurement system during a readout of an optical coding with a digital camera, FIG. 3 shows a highly simplified longitudinal section of the gas measurement system during a detection of a color change of a reaction substance with the digital camera, FIG. 4 shows an additional highly simplified longitudinal section of the gas measurement system during a readout of the optical coding with the digital camera, FIG. 5 shows a perspective view of the reaction support unit and a servomotor with driving roller, FIG. 6 shows a side view of the digital camera, of the reaction support unit with an indicator pin in a first position, and of the reaction support unit with the indicator system in a second position, FIG. 7 shows a perspective view of the indicator system in the first position and of the indicator system in the second position, FIG. 8 shows a longitudinal section of a suction pump with gas connector in a first position and of a portion of the reaction support unit, and FIG. 9 shows a longitudinal section of the suction pump with gas connector in a second position and of a portion of the reaction support unit.

Like reference symbols in the various drawings indicate like elements.

DETAILED DESCRIPTION

A gas measurement system 1 is used for measuring or detecting the concentration of gaseous and/or vaporous components. In a gas measurement arrangement 1 or a remaining gas measurement system 1, an exchangeable reaction support unit 2 is introduced manually by hand by a user. In the process, the gas measurement system 1 is a small, portable device which can be used in a mobile manner due to its energy supply by a battery. On a housing 25 of the remaining gas measurement system 1, a pump 11 designed as a suction pump 12 is arranged, which represents a gas conveyance device 10, FIG. 9. The housing 25 moreover forms a friction bearing for the movable reaction support unit 2. By means of a motor 13, for example, an electric motor 14 designed as a servomotor 15, and a driving roller 16 which can be set in rotation by the servomotor 15, the reaction support unit 2 can be moved within the housing 25, since a mechanical contact or a connection exists between the driving roller 16 and the reaction support unit 2, FIG. 5. Furthermore, on the remaining gas measurement system 1, a digital camera 17, LEDs 27 as transmission device 26, and color filter 28 are arranged, FIG. 4.

The reaction support unit 2 comprises a chip 21 or a plate 21, which is light permeable. On a top side of the chip 21, shown in FIG. 5, ten tubes 4 designed as glass tubes 5 are arranged, so that the tubes 4 delimit a channel 3, and an identical reaction substance 6 is arranged, within this channel 3 or within the tube 4, in the ten glass tubes 5, FIG. 8. At an end of the glass tubes 5 represented in FIG. 5 on the right, said glass tubes have an intake opening 7, and at an end of the glass tubes 5 on the left in FIG. 5, they have a discharge opening 8. The intake and discharge openings 7, 8 are here sealed in a fluid-proof manner by a seal 9, for example, a glass seal 9, in the form of a film, FIG. 8. As a result, it is ensured that the reaction substance 6 (FIGS. 7 and 8) within the glass tubes 5, prior to the gas mixture being passed through the tubes 4 by means of the suction pump 12, does not undergo a color change on the reaction substance 6 or the reaction substances 6, due to an unintended or uncontrollable exposure of the reaction substance to gas or vapor components. For example, the reaction substance 6 is used for detecting acetone, so that when a mixture with acetone is passed through, a color change on the reaction substance 6 occurs. In the area of the discharge openings 8, an indicator pin 23 is arranged in each case. Thus, one indicator pin 23 is associated with each one of the ten glass tubes 5. Furthermore, on the top side of the chip 21, an optical coding 22 is also present.

On the suction pump 12, a gas connector 18 is arranged, and on a support ring 19 enclosing the gas connector 18, on the bottom side, a resilient sealing ring 20, for example, a rubber or sealing ring 20, is applied to or attached to the support ring 19 (FIGS. 8 and 9). The support ring 19, in addition, has, perpendicularly to the plane of the drawing of FIGS. 8 and 9 (not shown), an enlargement in the form of an indicator pin movement element. In FIG. 8, a first position of the suction pump 12 with the gas connector 18 is represented, and in FIG. 9 a second position of the suction pump 12 with the gas connector 18 is represented. In the first position according to FIG. 8, no gas can be suctioned by the suction pump 12 through the glass tubes 5, and the seal 9 continues to be closed. During movement of the suction pump 12 with the gas connector 18, the sealing ring 9 is first broken or perforated by the gas connector 18, and subsequently the sealing ring 20 is placed outside on the top side onto the chip 21 and the glass tube 5, so that the opening inserted in the seal 9 is sealed off completely. In addition, an additional connector (not shown) perforates and opens the seal 9 on the corresponding intake opening 7 of the glass tube 5, so that the gas mixture can flow into the glass tube 5 through the intake opening 7. Subsequently, the suction pump 12 is activated, and as a result the gas mixture is suctioned in through the intake opening 7, it is subsequently led around the reaction substance 6 or the reaction substance 6 is exposed to the gas mixture, and subsequently the gas mixture is conveyed again into the surrounding environment, through the discharge opening 8, the gas connector 18, and the suction pump 12.

For the detection of acetone using the gas measurement system 1, the reaction support unit 2 is first introduced manually into a slot on the housing 25 up to a predetermined abutment (FIG. 1). Subsequently, the servomotor 15 moves the reaction support unit 2 into the position represented in FIGS. 2 and 4. In FIGS. 1-4, for simplicity's sake, only a portion of the glass tubes 5 is represented. Here, on the remaining gas measurement system 1 on the housing 25 beneath the chip 21, the transmission device 26 with LEDs 27 and a color filter 28 are arranged. For the readout of the optical coding 22 with the digital camera 17, the LEDs 27 are switched on, and owing to the light permeability of the chip 21, the optical coding 22 can thus be illuminated, and thus it can be read better optically by the digital camera 17. Subsequently, the servomotor 15 moves the reaction support unit 2 in a position so that the gas connector 18 is arranged above the discharge opening 8 of a first glass tube 5. The acquisition of the position of the reaction support unit 2 here also occurs simply by means of the digital camera 17, since the evaluating device has a corresponding optical software by means of which the position of the reaction support unit 2 can be detected on the basis of the data acquired by the digital camera 17. Subsequently, the suction pump 12 is moved together with the gas connector 18 downward, so that as a result the gas connector 18 perforates the seal 9, and the gas mixture can be suctioned through the discharge opening 8. In the process, an enlargement or indicator pin movement element—not shown—of the support ring 19 in addition moves the indicator pin 23, from a first position according to the upper chip 21 in FIG. 6 into a second position according to the lower chip in FIG. 6. In the first position of the indicator pin 23, the latter sticks farther out of the chip 21 than in the second position. The position of the indicator pin 23 can also be detected with the digital camera 17. The indicator pin 23 is of a different color, for example, orange, than the remaining reaction support unit 2; for example, the chip 21 is colored blue. The digital camera 17 here has two separate ROIs (region of interest) 24, so that the ROI 24 which is in the upper position in FIG. 7 in the first position in the upper ROI 24 the color orange occurs, and in the second position in the upper ROI 24 no or a substantially smaller quantity of the color of the indicator pin 23 occurs in the upper ROI 24. As a result, it is possible to detect by means of the optical evaluation software of the evaluating device whether an indicator pin 23 is in the first or second position. On the basis of this detection of the first or second position of the indicator pin 23, the reaction support unit 2 is moved furthermore in a self actuating manner and automatically by the servomotor 15 in a position such that the first, so far unused, glass tube 4, through which so far no gas mixture has been led, is located with the discharge opening 8 above the gas connector 18, and it is only subsequently that the suction pump 12 and the gas connector 18 are moved downward.

After passing the gas mixture through the glass tube 5, if the concentration of acetone as gaseous and/or vaporous component is sufficient, a color change occurs on the reaction substance 6 within the glass tube 5. This color change is detected by the digital camera 17 in a large number of separate positions, for example, 30 different positions, as a function of time. Due to the large pixel number of the digital camera 17 and the evaluation of the data supplied by the digital camera 17, this can be done simply by the optical evaluation software in the evaluating device. These data supplied by the digital camera 17 are stored in a data storage device, and it is only after the completion of the color change and the complete passage of the gas mixture through the glass tube, that an evaluation of the data acquired by the digital camera 17 is carried out, with a view to determining the color change on the reaction substance 6. If a predetermined concentration of acetone is exceeded, a warning signal is issued by a indicator device which is not shown.

During the detection of the color change of the reaction substance 6 with the digital camera 17, the display device 26 is switched on furthermore, and, due to the color filter 28, only electromagnetic radiation within a predetermined frequency range reaches the reaction substance 6, because the chip 21 is light permeable and the glass tube 5 is transparent. As a result, illumination of the reaction substance 6 occurs during the color change and the detection with the digital camera 17, resulting in a more precise and better determination of the color change by means of the digital camera 17.

In a further embodiment example—not shown—of the gas measurement system 1, different reaction substances for different gaseous and/or vaporous components are arranged in each of the ten glass tubes 5. After inserting the reaction support unit 2 and after reading the matrix coding 22, on which this is stored appropriately, namely that different reaction substances are arranged in the glass tube 5, then one after the other, independently, all ten glass tubes 5 are exposed to the passage of a gas mixture through them by the suction pump 12, analogously to the above—explained embodiment example, and the color change is detected by the digital camera 17. As a result, in this embodiment example, ten different gaseous and/or vaporous components can be detected by the gas measurement system 1.

All things considered, there are many advantages provided by the gas measurement system 1. By means of the digital camera 17, the color change on the reaction substance 6 can be detected at a large number of separate places, so that the accuracy of the evaluation and of the detection of the concentration of components is considerably increased. In addition, with the digital camera 17, the position of the reaction support unit 2 within the remaining gas measurement system 1 and also the position of the indicator pins 23 can be detected, so that as a result, advantageously, no additional devices are required.

Further, a gas measurement system 1 for measuring the concentration of gaseous and/or vaporous components of a gas mixture by means of a color change of at least one reaction substance 6 on a reaction support unit 2 is provided, wherein the at least one reaction substance 6 on the reaction support unit 2 is arranged separately within at least two light permeable channels 3. Therein, the gas measurement system 1 can comprise a gas conveyance device 10 for conveying the gas mixture through a channel 3 and to the at least one reaction substance 6; a mechanical bearing, in particular a friction bearing, for the reaction support unit 2; preferably a motor 13 for moving the reaction support unit 2 or another component, so that the gas mixture can be conveyed separately through one of the at least two channels 3; an optoelectronic detection device for detecting a color change of the at least one reaction substance 6 during and/or after the conveyance of the gas mixture through a channel 3, wherein the color change can be detected in the direction of flow of the gas mixture through the channel 3 in at least two separate positions; an evaluating device for evaluating the data detected by the optoelectronic detection device; an optical and/or acoustic display device for displaying the data evaluated by the evaluating device, wherein the optoelectronic detecting device is designed as a digital camera 17 with an electronic image converter or image sensor and an imaging optics system, preferably a lens system. In such a Gas measurement system, the digital camera 17 can be designed as a camera chip, in particular a CMOS camera chip. Also, this gas measurement system 1 can comprise a transmission device 26, for example, an LED 27, for the emission of electromagnetic radiation, so that electromagnetic radiation can radiate through and/or onto the at least one reaction substance 6; and/or the gas measurement system 1 can comprise a housing 25, and the housing 25 preferably in addition forms the friction bearing for the reaction support unit (2). Further, the gas conveyance device 10 can be designed as a pump 11, in particular a suction pump 12; and/or the gas measurement system 1 can comprise a gas connector 18 which can be moved between two positions, and which is fluidically connected to the gas conveyance device 10, so that, in a first position of the gas connector 18, no fluidic connection between the gas connector 18 and a channel 3 exists, and in a second position of the gas connector 18, a fluidic connection between the gas connector 18 and the channel 3 exists. In such a gas measurement system 1, the motor 13 can be designed as an electric motor 14, in particular a servomotor 15, and the motor 13 preferably can be brought into an effective mechanical connection with the reaction support unit 2 by means of a driving roller 16; and/or the evaluating device can comprise a processor, for example, a microcontroller, and a data storage unit; and/or the display unit can comprise a monitor and/or a light emitter, for example, a lamp or an LED, and/or a signal tone generator. Such a gas measurement system 1, in addition to the remaining gas measurement system 1, can comprise the reaction support unit 2, and the reaction support unit 2 can preferably comprise a chip 21 or a plate, and tubes 4, particularly glass tubes 5, arranged on the chip 21 or the plate, which delimit the channels 3, and the at least one reaction substance 6 is arranged within the tubes 4. Further, in such a gas measurement system 1, the reaction support unit 2 can comprise a coding 22, for example, a coding that can be read out optically, in particular a matrix coding, or an RFID chip; and/or the reaction support unit 2 can comprise two indicator pins 23 which can be moved between two positions, and one indicator pin 23 is associated with each tube 4, so that, in a first position of the indicator pin 23, the reaction substance 6 which has not been exposed to the gas mixture within the associated tube 4 can be indicated, and, in the second position of the indicator tube 23, the reaction substance 6 which has been exposed to the gas mixture within the associated tube 4 can be indicated; and/or the digital camera 17 can be arranged at a distance between 2 and 50 mm, particularly between 15 and 20 mm, from the tube 4 which is detected by the digital camera 17.

Also, the gas measurement system 1 can carry out a method for operating a gas measurement system 1, with the steps: preferably moving a reaction support unit 2 or another component with a motor 13; conveying a gas mixture through a, in particular only one, channel 3 with at least one reaction substance 6 by means of a gas conveyance device 10; detecting a color change by means of an optoelectronic detection device for detecting the at least one reaction substance 6 during and/or after the conveyance of the gas mixture through the channel 3, wherein the color change is detected in the direction of flow of the gas mixture through the channel 3 in at least two separate positions; evaluating the data acquired by the optoelectronic detection device with regard to the color change by means of an evaluating device; optical and/or acoustic display of the data evaluated by the evaluating device by means of a display device, characterized in that the color change is detected with a digital camera 17. In such a method, the digital camera 17 can detect, in particular exclusively, the colors red, green and blue, and/or the digital camera 17, in particular only one digital camera 17, in the direction of flow of the gas mixture through the channel 3, can detect the color change separately on a large number, for example, at least 5, 10, 50, 100 or 500, of separate positions; and/or the digital camera 17 can detect the course over time of the color change during and/or after the conveyance of the gas mixture through the channel 3, and preferably stores it in a data storage unit; and/or the digital camera 17, in particular only one digital camera 17, can detect the color change on the reaction substance 6 on a fictitious line in the direction of flow of the gas mixture over the entire fictitious line. Further, in said method, the digital camera 17 can detect the position of the reaction support unit 2 moved by the motor 13, by evaluating data from an image sensor of the digital camera 17, in particular by means of appropriate software on the evaluating device, and preferably the motor 13 can be controlled depending on the position detected with the digital camera 17. Also, in said method, for the fluidic connection of the gas conveyance device 10 to the channel 3, a gas connector 18 is moved on or in the channel 3, and/or before and/or during the conveyance of the gas mixture through the channel 3, an indicator pin 23 associated with the channel 3 is moved on the reaction support unit 2 from a first position into a second position, in particular by having the gas connector 18 brought in contact with the indicator pin 23 during a movement of the gas connector 18, so that, as a result, the indicator pin 23 is moved, in particular pushed, from the first into the second position. Additionally, in said method, the digital camera 17 can detect the position of the indicator pin 23, in order to detect that no gas mixture has been led through the channel 3 with the reaction substance, channel which is associated with the indicator pin 23, or that a gas mixture has already been passed through. Also, in said method, the digital camera 17 can read out an optical coding 22, in particular a matrix coding, on the reaction support unit 2, and, preferably as a function of the data stored in the coding 22, the color change of the reaction substance 6 detected by the digital camera 17 is evaluated. Further, the reaction support unit 2 can be introduced, for example, inserted or pushed, into the remaining gas measurement system 1, and this is detected by the digital camera 17, subsequently the optical coding 22 is read out by the digital camera 17 and/or the motor 13 is controlled depending on the position detected by the digital camera 17, and also on the basis of the detection of the position of the indicator pin 23, so that the reaction support unit 2 is moved into a position in which, during a movement of the gas connector 18, the gas connector 18 is brought into a fluidic connection with a channel 3 through which no gas mixture has been led.

LIST OF REFERENCE NUMERALS

1 Gas measurement system
2 Reaction support unit
3 Channel
4 Tube
5 Glass tube
6 Reaction substance
7 Intake opening on glass tube
8 Discharge opening on glass tube
9 Seal
10 Gas conveyance device
11 Pump
12 Suction pump
13 Motor
14 Electric motor
15 Servomotor
16 Driving roller
17 Digital camera
18 Gas connector
19 Support ring on gas connector
20 Sealing ring
21 Chip, plate
22 Optical coding
23 Indicator pin
25 ROI
26 Housing
27 Transmission device
28 LED
29 Color filter One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

The invention claimed is:

1. An apparatus comprising:
a housing defining a slot;
a friction bearing within the slot configured to couple to a reaction support unit, the reaction support unit comprising at least two light permeable channels configured to receive at least one reaction substance, the at least one reaction substance changing color in presence of at least one particular gaseous or vaporous component;
a gas conveyance device configured to convey gas through at least one channel of the reaction support unit;
an optoelectronic detection device configured to detect a color change of the at least one reaction substance on the reaction support unit during and/or after the conveyance of the gas mixture, the color change being detected in the direction of flow of the gas mixture through the at least two channels in at least two separate positions, the optoelectronic detecting device comprising a digital camera having an image converter or an imaging optics system;
an evaluating device configured to evaluate the data detected by the optoelectronic detection device; and
a sensory feedback device configured to provide sensory feedback characterizing the data evaluated by the evaluating device.

2. An apparatus as in claim 1, wherein the evaluating device comprises at least one data processor and a data storage unit.

3. An apparatus as in claim 2, wherein the at least one data processor comprises a microcontroller.

4. An apparatus as in claim 3, wherein the sensory feedback device comprises at least one of: a monitor, a light emitter, a lamp, an LED, and a signal tone generator.

5. An apparatus as in claim 1, wherein the imaging optics system comprises at least one lens system.

6. An apparatus as in claim 1, wherein the digital camera comprises at least one camera chip.

7. An apparatus as in claim 6, wherein the camera chip comprises a CMOS camera chip.

8. An apparatus as in claim 1, further comprising a transmission device configured to emit electromagnetic radiation through and/or onto the at least one reaction substance.

9. An apparatus as in claim 8, wherein the transmission device comprises a light emitting diode (LED).

10. An apparatus as in claim 1, wherein the housing forms the friction bearing for the reaction support unit.

11. An apparatus as in claim 1, wherein the gas conveyance device comprises at least one pump.

12. An apparatus as in claim 11, wherein the at least one pump comprises at least one suction pump.

13. An apparatus as in claim 1, further comprises a gas connector configured to be moved between two positions, and which is fluidically connected to the gas conveyance device, so that, in a first position of the gas connector, no fluidic connection between the gas connector and one of the channels exists, and in a second position of the gas connector, a fluidic connection between the gas connector and one of the channels exists.

14. An apparatus as in claim 1, further comprising a motor configured to move the reaction support unit within the slot so that the gas mixture can be conveyed separately through one of the at least two channels of the reaction support unit.

15. An apparatus as in claim 14, wherein the motor comprises an electric motor.

16. An apparatus as in claim 15, wherein the electric motor comprises a servomotor.

17. An apparatus as in claim 16, further comprising a driving roller to mechanically couple the motor with the reaction support unit.

18. An apparatus as in claim 1, further comprising the reaction support unit.

19. An apparatus as in claim 18, wherein the reaction support unit comprises a supporting surface with a plurality of tubes disposed therein that delimit the channels, and wherein the at least one reaction substance is arranged within the tubes.

20. An apparatus as in claim 19, wherein the supporting surface comprises a chip or a plate.

21. An apparatus as in claim 19, wherein the tubes comprise glass tubes.

22. An apparatus as in claim 18, wherein the reaction support unit further comprises an optical coding.

23. An apparatus as in claim 22, wherein the coding is selected from a group consisting of: a bar code, a matrix coding, and an RFID chip.

24. An apparatus as in claim 18, wherein the reaction support unit comprises two indicator pins that are configured to be moved between two positions with one indicator pin being associated with each tube, so that, in a first position of the indicator pin, a reaction substance that has not been exposed to the gas mixture within the associated tube can be indicated, and, in the second position of the indicator tube, a reaction substance that has been exposed to the gas mixture within the associated tube can be indicated.

25. An apparatus as in claim 19, wherein the digital camera is arranged at a distance between 2 and 50 mm from the tubes which is detected by the digital camera.

26. An apparatus as in claim 25, wherein the distance is between 15 and 20 mm.

27. A method comprising:
moving a reaction support unit through a gas measurement system, the reaction support unit having a plurality of channels each with at least one reaction substance;

conveying, using a gas conveyance device, a gas mixture through a single channel of the reaction support unit;
detecting, using a digital camera of an optoelectronic detection device, a color change of the at least one reaction substance during and/or after the conveyance of the gas mixture through the channel, wherein the color change is detected in the direction of flow of the gas mixture through the channel in at least two separate positions;
evaluating, using an evaluating device, data acquired by the optoelectronic detection device with regard to the color change; and
providing, using a sensory feedback device, sensory feedback regarding the evaluated data.

28. A method as in claim 27, wherein the reaction support is moved using a motor.

29. A method as in claim 27, wherein the digital camera exclusively detects colors comprising: red, green and blue.

30. A method as in claim 27, wherein the digital camera detects the color change on a plurality of positions.

31. A method as in claim 30, wherein the plurality of positions are more than 5 separate positions.

32. A method as in claim 31, wherein the plurality of positions are more than 10 separate positions.

33. A method as in claim 32, wherein the plurality of positions are more than 50 separate positions.

34. A method as in claim 32, wherein the plurality of positions are more than 100 separate positions.

35. A method as in claim 32, wherein the plurality of positions are more than 500 separate positions.

36. A method as in claim 27, further comprising:
detecting, by the digital camera over several time periods, a plurality of changes in color of the at least one reaction substance; and
storing the detected plurality of changes in color in a data storage unit.

37. A method as in claim 27, further comprising:
detecting, by the digital camera, the color change on the reaction substance on a fictitious line in the direction of flow of the gas mixture over the entire fictitious line.

38. A method as in claim 28, further comprising:
detecting a position of the reaction support unit using the digital camera;
wherein the motor moves the reaction support unit depending on a position detected by the digital camera.

39. A method as in claim 27, further comprising:
moving a gas connector on or in the channel to fluidically couple the gas conveyance device;
moving, before and/or during the conveyance of the gas mixture through the channel, an indicator pin associated with the channel on the reaction support unit from a first position into a second position by having the gas connector brought in contact with the indicator pin during a movement of the gas connector, so that, as a result, the indicator pin is moved from the first into the second position.

40. A method as in claim 39, wherein the digital camera detects the position of the indicator pin, in order to detect that no gas mixture has been led through the channel with the reaction substance, channel which is associated with the indicator pin, or that a gas mixture has already been passed through.

41. A method as in claim 27, further comprising:
reading, by the digital camera, at least one optical coding on the reaction support unit.

42. A method as in claim 41, wherein the optical coding is a matrix coding.

43. A method as in claim 41, wherein, as a function of the data stored in the coding, the color change of the reaction substance detected by the digital camera is evaluated.

44. A method as in claim 27, further comprising:
detecting, using the digital camera, a position of the reaction support unit as it advances into the gas measurement system;
positioning the reaction support unit so that gas can be selectively and separately conveyed into each of a plurality of individuals channel through which no gas mixture has been introduced.

45. A gas measurement system for measuring the concentration of gaseous and/or vaporous components of a gas mixture by means of a color change of at least one reaction substance on a reaction support unit, wherein the at least one reaction substance on the reaction support unit is arranged separately within at least two light permeable channels, the gas measurement system comprising
a gas conveyance device for conveying the gas mixture through a channel and to the at least one reaction substance;
a mechanical bearing for the reaction support unit;
a motor for moving the reaction support unit or another component, so that the gas mixture can be conveyed separately through one of the at least two channels;
an optoelectronic detection device for detecting a color change of the at least one reaction substance during and/or after the conveyance of the gas mixture through a channel, wherein the color change can be detected in the direction of flow of the gas mixture through the channel in at least two separate positions;
an evaluating device for evaluating the data detected by the optoelectronic detection device;
an optical and/or acoustic display device for displaying the data evaluated by the evaluating device;
wherein:
the optoelectronic detecting device is designed as a digital camera with an electronic image converter or image sensor and an imaging optics system.

* * * * *